United States Patent [19]

Sasaki et al.

[11] Patent Number: 5,789,047
[45] Date of Patent: Aug. 4, 1998

[54] FLEXIBLE, MULTILAYERED TUBE

[75] Inventors: Fumihiro Sasaki, Okayama-Ken; Hiroshi Shinmen, Okayama; Akira Suzuki, Uenohara-machi; Keiichi Arai, Hachioji, all of Japan

[73] Assignees: Japan GORE-TEX, Inc; Olympus Optical Co., both of Tokyo, Japan

[21] Appl. No.: 569,897

[22] Filed: Dec. 8, 1995

Related U.S. Application Data

[63] Continuation of Ser. No. 178,371, Dec. 21, 1993, abandoned.

[51] Int. Cl.[6] .................................................. B29D 22/00
[52] U.S. Cl. ................ 428/36.91; 428/36.9; 428/36.5; 428/304.4; 428/306.6; 428/308.4; 428/314.8; 128/4; 128/DIG. 4
[58] Field of Search ............................... 428/36.5, 36.9, 428/36.92, 304.4, 306.6, 308.4, 314.8, 36.91; 128/4, DIG. 14

[56] References Cited

U.S. PATENT DOCUMENTS

| 3,734,139 | 5/1973 | Zafiroglu | 138/146 |
|---|---|---|---|
| 4,194,041 | 3/1980 | Gore et al. | 428/252 |
| 4,279,245 | 7/1981 | Takagi et al. | 128/4 |
| 4,304,010 | 12/1981 | Mano | 623/1 |
| 4,347,204 | 8/1982 | Takagi et al. | 264/127 |
| 4,443,511 | 4/1984 | Worden et al. | 428/198 |
| 4,613,544 | 9/1986 | Burleigh | 428/315.5 |
| 4,619,641 | 10/1986 | Schanzer | 604/8 |
| 4,687,482 | 8/1987 | Hanson | 623/1 |
| 4,764,560 | 8/1988 | Mitchell | 524/506 |
| 4,816,339 | 3/1989 | Tu et al. | 428/421 |
| 4,882,113 | 11/1989 | Tu et al. | 264/127 |
| 4,925,710 | 5/1990 | Buck et al. | 428/34.5 |
| 4,945,125 | 7/1990 | Dillon et al. | 524/427 |
| 4,955,899 | 9/1990 | Della Corna et al. | 623/1 |
| 5,061,276 | 10/1991 | Tu et al. | 623/1 |
| 5,071,609 | 12/1991 | Tu et al. | 264/119 |
| 5,100,422 | 3/1992 | Berguer et al. | 606/151 |
| 5,104,400 | 4/1992 | Berguer et al. | 264/132 |

FOREIGN PATENT DOCUMENTS

| 0256748 | 8/1987 | European Pat. Off. . |
|---|---|---|
| 0269449 | 11/1987 | European Pat. Off. . |
| 5536492 | 5/1976 | Japan . |
| 54-74514 | 6/1979 | Japan . |
| 59-25725 | 2/1984 | Japan . |
| 6140328 | 7/1984 | Japan . |
| 2126827 | 2/1989 | Japan . |

*Primary Examiner*—James J. Seidleck
*Assistant Examiner*—Michael A. Williamson
*Attorney, Agent, or Firm*—Wayne D. House

[57] ABSTRACT

A flexible, multilayered tube with superior chemical resistance, heat resistance, and airtightness, as well as superior flexibility and resistance of the inner surface to staining. The tube comprises a flexible, multilayered tube having a first layer comprised of a non-porous polytetrafluoroethylene structure and a second layer comprised of a porous polytetrafluoroethylene structure laminated onto the outer peripheral surface of said first layer. The tube is useful as a medical tubing and in particular useful as an endoscope tube.

25 Claims, 6 Drawing Sheets

FLEXIBLE, MULTILAYERED TUBE

This application is a continuation, of application Ser. No. 08/178,371 filed Dec. 21, 1993, now abandoned.

FIELD OF THE INVENTION

The present invention pertains to a flexible, multilayered tube, especially to a flexible, multilayered tube with a superior flexibility required for small bending radii.

BACKGROUND OF THE INVENTION

Various multilayered tubes offering excellent flexibility are previously known. For example, a multilayered flexible tube comprised of an inner layer with a porous structure consisting of polytetrafluoroethylene (hereinafter referred to as PTFE) laminated with an outer layer with a porous structure comprised of PTFE via an interlayer comprised of an airtight, flexible plastic on the outer peripheral surface of said inner layer is described by Japanese Kokoku Pat. No. Sho 59[1984]-49464. In this flexible, multilayered tube, the inner layer is comprised of PTFE with a porous structure, so the flexibility for small bending radii is superior but the chemical resistance and heat resistance of the plastic used for the interlayer are poor in comparison to PTFE. Therefore, cracks and pinholes are likely to form in the plastic layer, and as a result, the airtightness of the material is lost. When the airtightness of the interlayer is lost, the inner layer and outer layer of the tube become air permeable because of the porous structure of such inner layer and outer layer; therefore, it is not possible to use the tube as an airtight tube.

Additionally, a multilayered tube comprised of an inner layer made of a fluorine resin with a non-porous structure, such as tetrafluoroethylene/hexafluoropropylene copolymer (FEP), and an outer layer comprised of a porous PTFE structure, has been suggested in Japanese Kokoku Patent No. Sho 55[1980]-36492. However, in the case of this multilayered tube, the flexibility of the FEP with a non-porous structure that comprises the inner layer, in which the bending radius becomes smallest when bent, is insufficient. Therefore, when the tube is bent with a small bending radius, there is the problem of kinking.

Still further, in Japanese Kokai Patent Application No. Hei 2[1990]-126827, a conduit comprised of a drawn foam PTFE in which the inner surface of the material is heated above the melting point of PTFE, is melted to improve the sliding properties of the inner surface. However, in this conduit only the inner surface of the drawn foam tube is melted, so it is not possible to produce a uniform, continuous layer of molten material. Furthermore, the airtightness of the tube itself can be improved, but it is difficult to produce a completely airtight structure, and the resistance to staining of the inner surface is still insufficient.

SUMMARY OF THE INVENTION

The present invention results in a flexible, multilayered tube with superior chemical resistance, heat resistance, and airtightness, as well as superior flexibility and resistance of the inner surface to staining.

According to the present invention, it is possible to produce a flexible, multilayered tube comprising of a first layer comprised of a non-porous polytetrafluoroethylene structure and a second layer comprised of a porous polytetrafluoroethylene structure laminated onto the outer peripheral surface of said first layer; the first layer and the second layer are laminated by means of fusion under heat, with the thickness of the first layer being 1/1000 to 1/2 of the combined thickness of the first layer and second layer.

Furthermore, according to the present invention, it is possible to produce a flexible, multilayered tube consisting of a first layer comprised of a non-porous polytetrafluoroethylene structure and a second layer comprised of a porous polytetrafluoroethylene structure laminated onto the outer peripheral surface of the first layer; the first layer and second layer are laminated via an adhesive interlayer between them, with the thickness of the first layer being 1/1000 to 1/2 of the combined thickness of the first layer and second layer.

The material used for the first layer and the material used for the second layer of the flexible, multilayered tube of the present invention is PTFE, which has superior chemical resistance and heat resistance. Furthermore, the first layer of the tube of the present invention is comprised of a non-porous PTFE structure and the second layer is comprised of a porous PTFE structure.

DETAILED DESCRIPTION OF THE INVENTION

The non-porous PTFE structure film can be produced by the methods described below.

(1) A mixture comprised of a PTFE resin having an approximate degree of crystallinity greater than 95%, and a liquid lubricant (naphtha solvent, white oil, etc.) is processed from an extruder as a film, then dried to produce a porous PTFE film structure. When the extruded film is dried, the liquid lubricant in the film evaporates and micropores are formed in the film, producing a porous film structure with an approximate porosity of 30%. When the porous film structure produced in said manner is baked, the film contracts under heat and the micropores in the film close due to thermal contraction of the film, producing a non-porous film structure.

(2) Alternatively, after drying or without drying the extruded film containing the liquid lubricant, the film is drawn in the biaxial or uniaxial direction at a high rate of greater than 10% per second under nonbaking conditions at a temperature below 327° C. to produce a porous PTFE film structure. When pressure is applied to the drawn, porous film structure produced as described above, a non-porous PTFE film structure can be formed. The drawn film subjected to said pressure treatment may be either a baked film produced by a heat treatment at a temperature above the melting point of PTFE, or a nonbaked film.

Production of the porous PTFE film is also explained in detail in Japanese Kokoku Patent No. Sho 51[1976]-18991 and Japanese Kokoku Patent No. Sho 56[1981]-17216.

As an example of the method used to make the porous PTFE film into a non-porous structure by applying pressure, a method consisting of placing a porous PTFE film between a pair of synthetic resin sheets such as polyester film sheets and passing said film sheets between pressure rollers, or a method consisting of placing the porous PTFE film between a pair of metal foils such as aluminum foil and passing said film between pressure rollers heated to a temperature above the melting point of the PTFE, can be mentioned. In the former method described above, the temperature used is selected to be between ambient temperature and a temperature below the melting point of the synthetic resin used. As for the pressure used, it varies depending on factors such as the modulus of the rollers used, but in general, a pressure greater than 50 kg/cm$^2$, preferably 100 to 250 kg/cm$^2$, is applied. Generally, pressure treatment can be performed at a lower pressure in the latter method than in the former method. In this method, the porous PTFE film is compressed to a thickness less than 80%, preferably less than 20 to 60%, of the thickness before compression, thereby making the film non-porous. Also, as a different method for making the porous PTFE film into a non-porous film, a method consisting of wrapping at least one layer of porous film onto the outer peripheral surface of a pipe, inserting the end of said material on the pipe through a ring or die opening having a diameter smaller than the outer diameter of the material, but greater than the outer diameter of the pipe, and pulling the material forcibly from the other end, can be used. In said method, the material is firmly compressed from the outer peripheral surface toward the center as the material passes through the opening, so the porous film that comprises said material becomes a non-porous film structure due to the compressive force applied. As for the diameter of the opening, it is desirable to have a diameter that makes it possible for the thickness of the film produced on the outer peripheral surface of the pipe to be less than 80%, preferably 20 to 60%, of the thickness before the compression treatment.

The non-porous film structure produced by subjecting the porous PTFE film structure to said compression treatment has a Gurley No. (the time required for 100 cm$^3$ of air to flow per 6.45 cm$^2$ area under a water column pressure of 12.4 cm) greater than 500,000 sec and is virtually an airtight material.

The thin PTFE film structures are preferred. In general, it is preferred to be less than 50 microns, and a range of 5 to 30 microns is further preferred. In said non-porous film structure, the entire film is comprised of virtually an airtight structure; therefore, excellent air impermeability can be achieved even when a thin film is used.

For the porous PTFE film structure used as the precursor material described above, either a uniaxially drawn or a biaxially drawn film is used, but a uniaxially drawn film is preferred, and the general pore structure of the film is 0.05 to 30 microns and more preferably 0.2 to 10 microns; with a porosity of 30 to 70% and more preferably 40 to 60%. The thickness of the film is preferably 20 to 200 microns, and more preferably 40 to 100 microns.

In order to produce the multilayered tube of the present invention, the PTFE film of the first layer material is wrapped around a core material and compressed into the form of a non-porous tube. For the first layer material, either a PTFE film having a non-porous structure or one that forms a non-porous structure upon baking is used. For the core material, materials having a melting point above the baking temperature used during the baking process are desirable, and those with good release properties and having a smooth surface with a low degree of protrusions are desirable so that the core material can be easily removed after the baking process. Also, when a material having a coefficient of thermal expansion greater than that of PTFE is used, removal is achieved after the baking treatment. For the method of wrapping the film around the core material, given methods may be used such as longitudinally wrapping the film around the core material to create a longitudinally oriented seam parallel to the longitudinal axis of the core material, or helically wrapping the film about the core material to create a spirally oriented seam. The nonbaked PTFE film has self-adhesive properties, so the film can be made non-porous without using an adhesive by simply applying pressure to the film. The inner diameter and thickness of the tube comprised of the first layer of PTFE film vary depending on the intended application of the tube, but generally the inner diameter is approximately 1 to 20 mm, and the thickness is less than 300 microns, preferably 50 to 200 microns. When the thickness of the film becomes greater than 300 microns, the flexibility of the tube produced upon hot-melt molding the film and baking deteriorates, and kinks are likely to occur. The number of film layers in the rolled film varies depending on the thickness of the film wrapped around, but in general 1 to 10 layers are applied. When the film is helically wrapped, it is desirable for the wrapping angle of the film around the core material to be less than 30° from a line normal to the longitudinal axis of the core material, and it is further desirable to form a greater wrapping pitch. When the film is wrapped in a spiral form of more than 2 layers, it is possible to eliminate the orientation in the film strength generated at the time of the extrusion and drawing processes by changing the wrapping direction or the wrapping angle of the film, thus a tube with a low orientation strength and superior tolerance to repeated torsion can be produced.

For the core material, pipes, wires, or bars comprised of materials such as metals, ceramics, or plastics can be used.

Subsequently, a porous PTFE film structure comprising the second layer of material is wrapped over the PTFE film of the first layer produced as described above and stabilized. In this case, rather than a biaxially drawn film, a uniaxially drawn film is desirable for the porous PTFE film structure. The use of a uniaxial film will result in a tube that is less likely to kink. Also, it is desirable to use a porous PTFE film structure having the following properties after lamination of the first and second layers: micropore diameter 0.05 to 30 microns, and more preferably 0.2 to 10 microns, and porosity of 30 to 70%, and more preferably 40 to 60%. When the porosity of the film is less than 30%, the flexibility of the tube produced deteriorates; on the other hand, when greater than 70%, the tube produced becomes too soft and the ability of the tube to retain its shape is reduced. For the method used to wrap the film, known methods such as longitudinally wrapping or helically wrapping can be used. In general, the thickness of the porous PTFE film tube structure described above is 100 microns to 2 mm, and more preferably 200 microns to 0.8 mm. When the thickness of the film is too thin, kinking is likely to occur in the multilayered tube; on the other hand, when too thick, the flexibility of the tube is reduced. The number of layers of the film wrapped around varies depending on the thickness of the film, but it is generally 2 to 20 layers.

When a porous PTFE film structure is used for wrapping as described above, two or more types of films with different properties can be used for said film. For example, a uniaxially drawn film and a biaxially drawn film can be alternately used, thus a multilayered tube with a superior tensile strength and pressure resistance can be produced. In the second layer, it is possible to change the wrapping direction and the wrapping angle of the film when the film is wrapped in a spiral fashion to form two or more layers, as in the case of the first layer.

It is desirable for the thickness of the first layer of film in the wrapped material produced by the method described above to have a ratio of $1/1000$ to $1/2$, preferably $1/100$ to $1/3$, of the combined thickness of the film materials of the first and second layers. When the thickness ratio is greater than $1/2$, kinking is likely to occur in the multilayered tube produced; on the other hand, when it is less than $1/1000$, the thickness of the first layer is too thin for the thickness of the second layer, therefore, rupturing of the first layer is likely to occur during use of the multilayered tube.

The wrapped PTFE film produced as described above is baked at a temperature above the melting point of the PTFE, preferably above 345° C., and ideally 350° to 370° C. The baking time is determined appropriately depending on the baking temperature and the thickness of the tube, but in general it is approximately 5 sec to 60 min. Upon baking, the wrapped PTFE films are melted and the films are bonded by lamination, producing a non-porous, multilayered tube structure. After baking, the core is removed and the target multilayered tube is produced. In the process for producing the multilayered tube described above, the porous film structure of the second layer material contracts upon baking and the stress generated forces contraction of the second layer toward the first layer, affecting the bonding of the laminated portion of the films. Also, a slight change occurs in the micropore structure of the PTFE film after baking compared with that before baking due to fusion and the contraction stress of the film upon baking, but a second layer with an adequate micropore structure can be produced regardless.

In the above, a method of producing a tube by wrapping PTFE films is explained, but in the present invention it is possible to use a tube material produced by extruding a mixture comprised of a PTFE resin and a liquid lubricant in tube form as the first layer material and/or second layer material. In order to produce the two-layered tube structure of the present invention with an extruded tube in combination with a tube formed from the rolled, flat film described above, a tube comprised of a first layer material that comprises the inner layer is inserted into a tube comprised of the second layer material that comprises the outer layer, with baking being performed under the same conditions as described above; thus, the inner layer and outer layer are laminated together. Also, when a tube comprised of a rolled flat film first layer material is inserted into a porous structure extruded tube, then baked, it is possible to produce the tube of the present invention.

As a method to produce a non-porous structure tube, in addition to the (1) baking method and (2) pressuring method using the precursor porous tube structure described above, the method described below can also be used.

A substance produced by dispersing a fine-powdered fluorine thermoplastic resin in a dispersion media is passed through a cavity in the inner layer porous tube structure and the pressure outside of the tube is kept lower than that inside the tube. In this manner, the dispersion that passes through the tube is drawn toward the circumference of the outer wall of the tube, and the dispersant in the dispersion seeps from the outer peripheral surface of the tube, but in this case the resin powder in the dispersion accumulates on the surface of the tube while clogging the micropores in the wall of the tube. When the filtration process of the dispersion is continued for a prescribed time through the wall of the tube, the micropores with a shallow depth from the inner wall of the tube are filled with the resin powder, which stops the seeping of the dispersant from the outer wall of the tube. The tube is dried at this point and baked. In this manner, a tube having an inner surface with a non-porous structure and an outer surface with a porous structure can be produced. In the wall of said tube, the thickness of the non-porous structure is 5 to 50%, preferably 10 to 30%, of the thickness of the tube wall.

For the fine fluorine thermoplastic resin powder used to manufacture the solid structure tube described above, for example, a fine fluorine resin powder such as polytetrafluoroethylene (PTFE), tetrafluoroethylene/perfluoroalkyl vinyl ether copolymer (PFA), tetrafluoroethylene/hexafluoropropylene copolymer (FEP), tetrafluoroethylene/hexafluoropropylene/perfluoroalkyl vinyl ether copolymer (EPE), tetrafluoroethylene/ethylene copolymer (ETFE), polychlorotrifluoroethylene (PCTFE), chlorotrifluoroethylene/ethylene copolymer (ECTFE), polyvinylidene fluoride (PVDF), and polyvinyl fluoride (PVF) can be mentioned. Among those described above, the use of PFA is especially desirable since properties such as the melting point, elongation (modulus of deformation), and coefficient of friction of the material are closest to that of the base material PTFE. As for the size of the resin powder, any size that causes clogging of the pores on the wall of the tube is suitable, with the average grain diameter being 0.1 to 2 times the diameter of the micropores in the wall of the tube, and with approximately 0.5 to 1 times the diameter being further desirable.

For the dispersant used for the resin powder described above, ethanol, methanol, isopropyl alcohol, acetone, etc., can be mentioned. The concentration of the resin powder in the dispersion is preferably 5 to 50% by weight, and more preferably 10 to 30% by weight. The pressure used for filtration of the dispersion inside the tube through the wall of the tube is preferably 0.05 to 1 atmospheres, and more preferably 0.1 to 0.5 atmospheres. The baking temperature used for the tube deposited with the resin powder on the inside surface is a temperature above the melting point of said resin powder. In general, it is a temperature of 300° to 330° C. Also, the thickness of the wall of the tube is preferably 50 to 700 microns, and more preferably 100 to 500 microns.

The tube having an inner surface with a non-porous structure and an outer surface with a porous structure produced by the method described above is used as the first layer material for the multilayer structured tube of the present invention, as well as a tube with an integrated first and second layer.

The entire flexible, multilayered tube of the present invention produced as described above is comprised virtually entirely of PTFE, therefore, the heat resistance and chemical resistance are superior. Furthermore, the thickness of the first layer is defined as 1/1000 to 1/2 of the combined thickness of the first and second layer, so a small bending radius can be easily achieved, and the flexibility is excellent.

Furthermore, in the multilayered tube of the present invention, the first layer is comprised of a non-porous PTFE structure. Therefore, film defects such as pinholes are less likely to occur, and air/liquid contact between the first layer and second layer is completely blocked. When the multilayered tube of the present invention is placed in a highly corrosive liquid or vapor, the tube is not subject to corrosion due to said liquid or vapor, and the liquid or vapor that contacts the surface of the second layer does not seep inside.

When the multilayered tube of the present invention is subjected to a small bending radius, for example, bending at a radius of 10 mm, excellent flexibility and elasticity are achieved, and when the material is bent a number of times kinking does not occur.

Furthermore, the first layer of said multilayered tube is comprised of a non-porous PTFE structure; therefore, qualities such as the sliding property, stain resistance, antifungal properties, and resistance to adsorption of organic materials are superior.

The flexible, multilayered tube comprised of a first layer and second layer of the present invention can be firmly bonded when an adhesive layer comprised of a fluorine thermoplastic resin is provided between the first layer and second layer to further improve the integration between such first layer and second layer. When a tube comprised of a first layer and second layer alone is subjected to bending a number of times under harsh conditions, separation at the interface between the first layer and second layer occurs, but when an adhesive layer comprised of a fluorine thermoplastic resin is provided between said layers, the problem is eliminated.

In order to produce a tube having an adhesive layer between the first layer and second layer, for example, (1) a dried PTFE film that forms a non-porous structure upon baking or (2) a non-porous PTFE film structure produced by applying pressure to a nonbaked porous PTFE film structure is used as the first layer material, said material is stabilized on the core material, then the fluorine thermoplastic resin film is wrapped around the outer peripheral surface of the material. For the second layer material, a porous PTFE film structure is then further wrapped around the outer peripheral surface.

As for the wrapping method, the film can be either longitudinally or helically wrapped about the core material. Subsequently, the film material produced as described above is baked. Thus, a multilayered tube with a first layer and second layer firmly integrated via an adhesive layer can be produced.

For the fluorine thermoplastic resin used as said adhesive layer material, one with a melting point lower than that of PTFE, for example, PFA, EPE, FEP, PCTFE, ETFE, ECTFE, PVDF, etc., can be mentioned. Among these, it is especially desirable to use PFA since the properties of the material are closest to those of the base PTFE material. As for the thickness of the fluorine thermoplastic resin film, thinner films are preferred, for example less than 25 microns, and most preferably less than 10 to 15 microns. The number of layers of the film in said film material is 1 to 3 layers. The fluorine thermoplastic resin film melts at a temperature lower than the baking temperature (melting temperature) of the PTFE; it flows into the micropores of the first layer material and/or second layer material, which provides an anchoring effect and further improves the integration between the first layer and second layer materials upon baking. In general, the thickness of the adhesive layer between the first layer and the second layer is preferably 5 to 75 microns, and more preferably, 10 to 20 microns.

In the flexible, multilayered tube of the present invention, when a tube comprised of multiple layers of PTFE film alone is used for the first layer, delamination at the interfaces between the layers of PTFE occurs when the material is subjected to bending a number of times under harsh conditions. Thus, the nonpermeability of the first layer is destroyed and permeability of the wall of the tube occurs. It was discovered that this problem was eliminated when the first layer material is deposited or is laminated with a fluorine thermoplastic resin film that forms an adhesive layer.

An integrated tube having a first layer comprised of multiple layers of PTFE film with the multiple PTFE film layers being bonded with adhesive layers can be made. For example, a two-layered film comprised of a PTFE film laminated with a fluorine thermoplastic resin film by the hot-melt method as the first layer material, is wrapped around a core material with the PTFE film facing the core material. The fluorine thermoplastic resin film that forms the adhesive layer between the first layer and second layer is optionally applied; the second layer material is further wrapped around the multiple PTFE film layers. Subsequently, the material produced as described above is baked. Thus, a tube can be produced having a first layer with multiple layers of PTFE film with each PTFE film layer firmly bonded via an adhesive layer comprised of a fluorine thermoplastic resin, the nonpermeability of which is retained even after bending many times under harsh conditions. Also, when the adhesive layer comprised of fluorine thermoplastic resin is provided between the first layer and second layer, a tube with a firmly bonded first layer and second layer can be produced.

The type of the fluorine thermoplastic resins used between each part of the multilayered PTFE film that comprises the first layer, and the thickness of said film, are the same as those described for the fluorine thermoplastic resin films used between the first layer and second layer described above.

As in the case of the first layer described above, a fluorine thermoplastic resin film can be provided between each of the multiple PTFE film layers that comprise the second layer.

Figure 1:
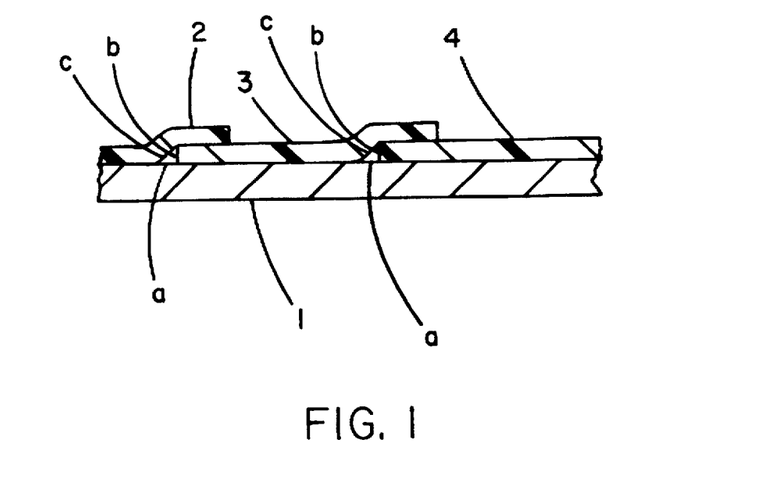
FIG. 1 is an explanatory cross section that shows the condition of the inner surface of the wrapped material produced upon helically wrapping a PTFE film around the core material.
Figure 2:
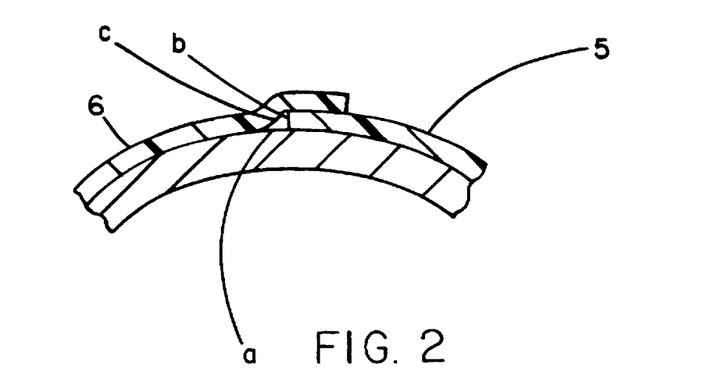
FIG. 2 is an explanatory cross section that shows the condition of the inner surface of the wrapped material produced upon longitudinally wrapping a PTFE film around the core material.

When a tube-form wrapped film is produced by wrapping the PTFE film of the first layer material onto a core material in either longitudinal or helically-oriented fashion, either a spiral-form or a straight-line groove is produced in the longitudinal direction on the inner surface of the tube as shown in FIG. 1 and FIG. 2. FIG. 1 is an explanatory cross section that shows the condition of the inner surface of the wrapped material when the PTFE film is rolled in the spiral fashion. FIG. 2 is an explanatory cross section that shows the condition of the inner surface of the wrapped material when the PTFE film is longitudinally wrapped. In these figures, 1 indicates the core material and 2, 3, 4, 5, and 6 indicate the PTFE film, and a indicates a wedge-shaped groove that stretches in the longitudinal direction.

As shown in FIG. 1 and FIG. 2, groove a is formed at end b of lower layer 3 or 5, and the lower surface c of the upper layer film 2 or 6 when the end of one film 2 or 6 is placed on the surface of the end of the other film 3 or 5. When the film is wrapped in a spiral fashion, groove a, which stretches along the longitudinal direction in a spiral form, is produced on the inner surface of the tube. When the film is longitudinally wrapped, groove a, stretching in a straight line in the longitudinal direction, is produced. The depth of groove a varies depending on the thickness of the film; in general, it is greater than 5 microns.

In the product tube formed with groove a at the inner surface (the inner surface of the first layer) as shown in FIG. 1 and FIG. 2, contaminants are likely to be trapped and accumulate during application, and when contaminants are trapped in the groove, it is difficult to remove such contaminants by washing.

The problems described above can be eliminated when a lapped or laminated material comprised of PTFE and a fluorine thermoplastic resin are used as the film, and when a two-layered film having a flange comprised of a fluorine thermoplastic resin film on one or both ends is used.

Figure 3:
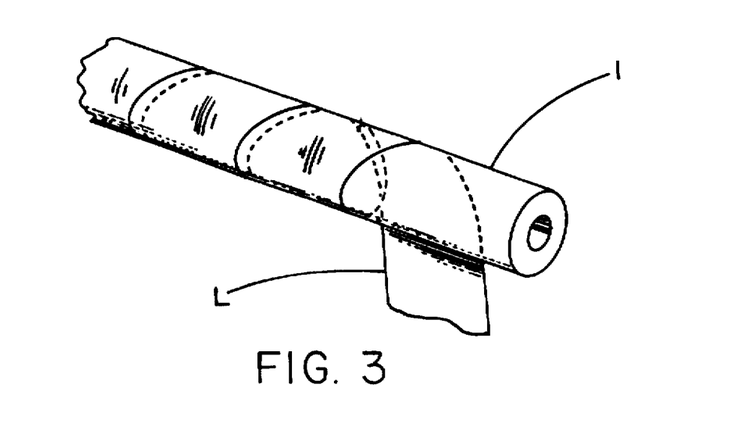
FIG. 3 shows production of the two-layered film on the core material in a helical fashion.
Figure 4:
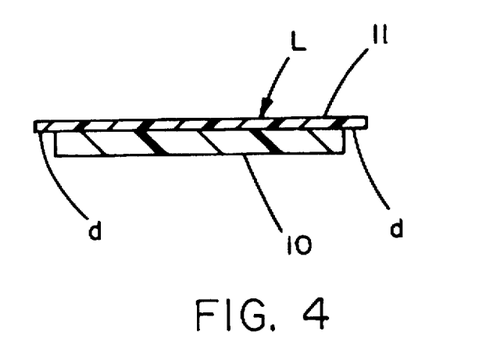
FIG. 4 is a cross section that shows the production of the two-layered film in a helical fashion.

FIG. 3 is an explanatory cross section that shows wrapping of the two-layered film on the core material in the spiral fashion. In FIG. 3, 1 is the core material and L is the two-layered film. As shown in FIG. 4, the two-layered film is comprised of PTFE film 10 and fluorine thermoplastic resin film 11, having flanges d on both ends.

Figure 5:
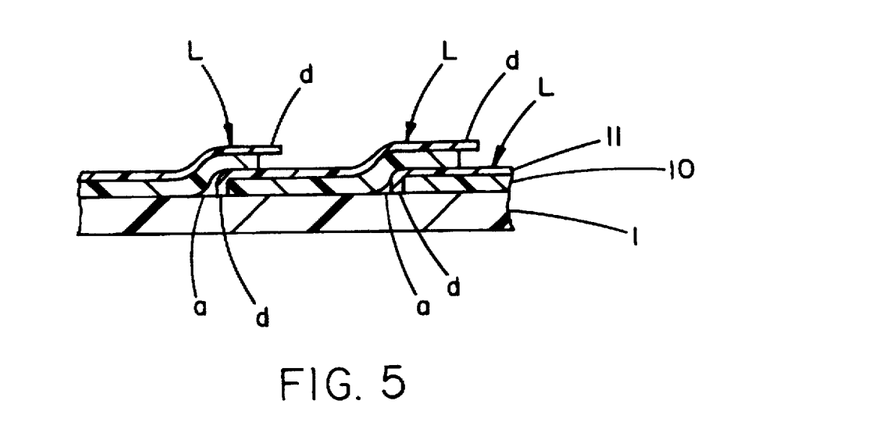
FIG. 5 is a cross section that shows the condition of the inner surface of the wrapped material produced upon wrapping the two-layered film around the core material in a helical fashion.

FIG. 5 is an explanatory cross section that shows the condition of the inner surface of the wrapped material when the two-layered film is wrapped around the core in a spiral fashion. In FIG. 5, 1 is the core material, L is the two-layered film, 10 is the PTFE film, and 11 is the fluorine thermoplastic resin film, with a representing the groove. The thickness of the fluorine thermoplastic resin film 11 is preferably ⅛ to 1 times, and more preferably ½ to 1 times, the thickness of PTFE film 10. Also, the width of flange d is less than 0.5 mm; in general, it is 0.01 to 0.4 mm. As shown in FIG. 5, one of the flanges d on the two-layered film L exists inside groove a.

Figure 6:
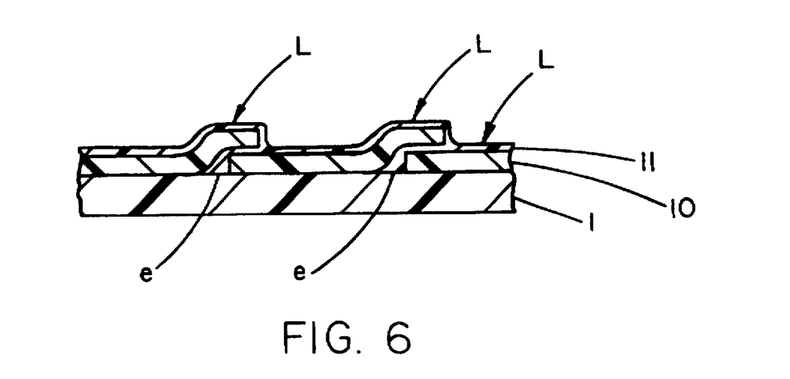
FIG. 6 is a cross section that shows the condition of the inner surface of the wrapped material produced by baking the material upon wrapping the two-layered film around the core material in a helical fashion.

FIG. 6 is an explanatory cross section that shows the condition of the inner surface of the baked product produced by baking the wrapped material shown in FIG. 5 at a temperature above the melting point of fluorine thermoplastic resin film 11, generally at 320° to 370° C.

As shown in FIG. 6, the fluorine thermoplastic resin film is melted upon baking, with groove a being filled with molten material e, producing a virtually smooth surface of the PTFE and fluorine thermoplastic resin.

Figure 7:
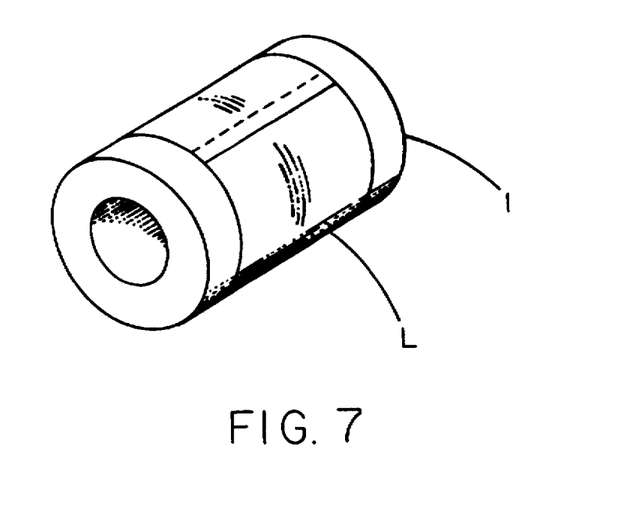
FIG. 7 is a perspective view that shows production of the two-layered film longitudinally wrapped about the core material.
Figure 8:
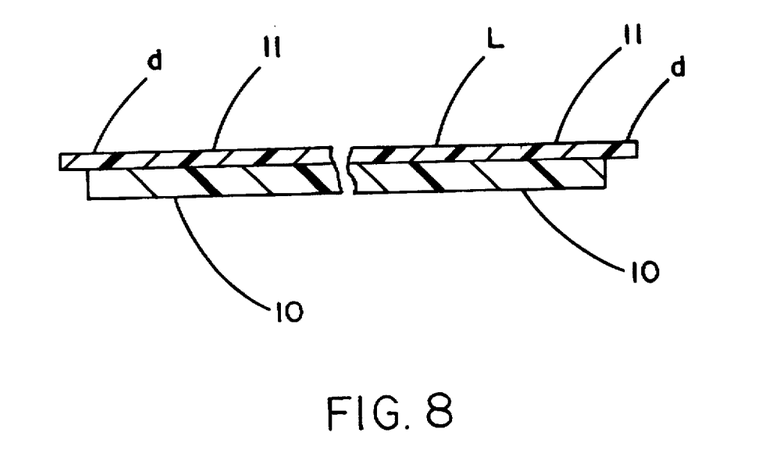
FIG. 8 is a cross section that shows the two-layered film used for longitudinal wrapping about the core material.

FIG. 7 shows a structural diagram of the two-layered film longitudinally wrapped around the core material to produce a longitudinally-oriented seam parallel to the longitudinal axis of the resulting tube. In FIG. 7, 1 is the core material two-layered film. As shown in FIG. 8, the two-layered film is comprised of PTFE film 10 and fluorine thermoplastic resin film 11, having flanges d on both ends.

Figure 9:
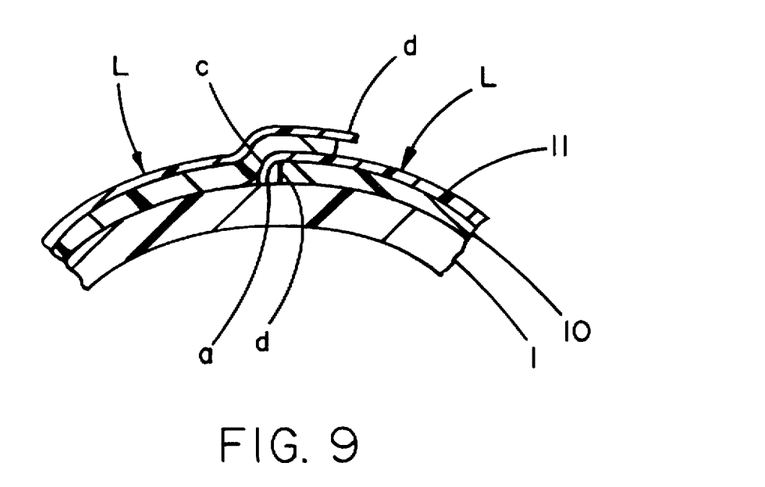
FIG. 9 is a cross section that shows the condition of the inner surface of the wrapped material produced upon longitudinal wrapping of the two-layered film around the core material.

FIG. 9 shows an explanatory cross section of two-layered film longitudinally wrapped around the core material. In FIG. 9, 1 is the core material, L is the two-layered film, 10 is the PTFE film, and 11 is the fluorine thermoplastic resin film, with a representing the groove. The thickness of the fluorine thermoplastic resin film 11 is ⅛ to 1 times, preferably, ½ to 1 times, that of the PTFE film 10. Also, the width of the flange d is preferably less than 0.5 mm; in general, it is most preferably 0.01 to 0.4 mm. As shown in FIG. 9, one of the flanges d on the two-layered film L exists inside the groove a.

Figure 10:
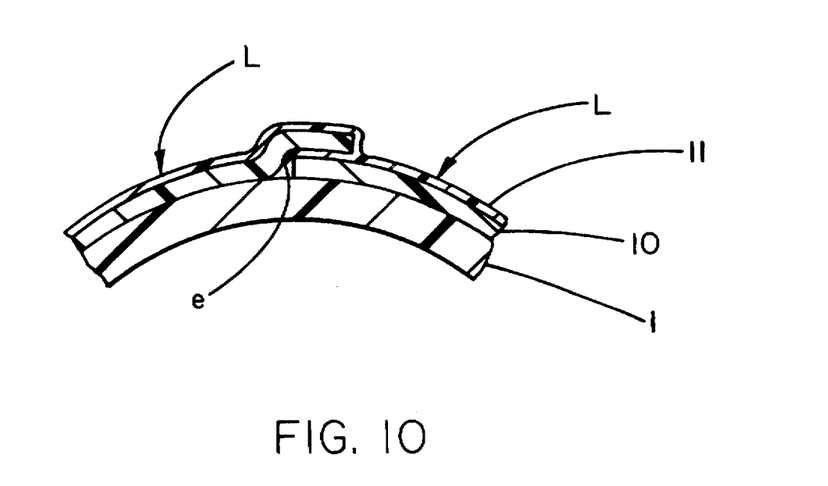
FIG. 10 is a cross section that shows the condition of the inner surface of the wrapped material produced by baking the material upon longitudinal wrapping of the two-layered film around the core material.

FIG. 10 is an explanatory cross section that shows the condition of the inner surface of the baked product produced by baking the wrapped material shown in FIG. 9 at a temperature above the melting point of fluorine thermoplastic resin film 11, generally at 320° to 370° C.

As shown in FIG. 10, the fluorine thermoplastic resin film is melted upon baking, with groove a being filled with molten material e, producing a virtually smooth surface of the PTFE and fluorine thermoplastic resin.

In the above, as an adhesive layer material deposited between the first layer and second layer and between multiple layers of film that comprise the first layer, a fluorine thermoplastic resin film was mentioned, but the adhesive layer material may be a fine-powdered fluorine thermoplastic resin. When the adhesive layer is produced from a fine powder, for example, the fine powder is dispersed in water or an organic solvent, then the dispersion produced is coated onto the PTFE film and dried, thus, an adhesive layer can be produced over the surface of the PTFE film. The average grain diameter of the fine powder in the dispersion is approximately 0.2 to 0.4 microns, and the concentration of the fine powder in the dispersion is preferably less than 50% by weight, and more preferably 10 to 30% by weight. The adhesive layer produced by the method described above is baked as in the case in which the fluorine thermoplastic resin adhesive film is used.

In the flexible, multilayered tube of the present invention described above, various types of layers may be further laminated over the outer peripheral surface to form a multilayered structure consisting of three or more layers, as needed.

Additionally, a third layer comprised of an airtight material can be deposited. Also, a fourth layer comprised of a porous PTFE structure can be further deposited to produce a flexible, multi-layered tube with a four-layered structure.

In order to produce the flexible, multilayered tube with the four-layered structure described above, for example, the flexible, multilayered tube of the present invention comprised of a first layer with a non-porous PTFE structure and a second layer with a porous PTFE structure is used as a base, with the third layer comprised of an airtight material being deposited around the outer peripheral surface of said tube. In this case, for the airtight material, conventional materials such as synthetic resin films and metal foils having a synthetic resin layer can be used. For the synthetic resins, fluorine resins such as FEP (tetrafluoroethylene/hexafluoropropylene copolymer), PFA (tetrafluoroethylene/perfluoroalkyl vinyl ether copolymer), polytetrafluoroethylene and fluoro-rubbers, and polyurethanes, polyimides, nylons, polyesters, polyvinyl chlorides, polyethylenes, and other polyolefins can be mentioned.

For metal foils, aluminum foil, copper foil, titanium foil, etc., can be mentioned. The metal foil having a synthetic resin layer can be produced by laminating a synthetic resin film or by coating a synthetic resin as described above, or by coating a conventional adhesive composition onto at least one surface of the metal foil and drying.

As a method used to deposit the airtight material layer onto the outer peripheral surface of the base tube, a method consisting of wrapping an airtight film material around a base tube with or without an adhesive, a method consisting of coating and drying the synthetic resin solution, or a method consisting of covering with a heat-shrunk synthetic resin tube, then performing heat-contraction, etc., can be mentioned. The thickness of the airtight material layer is preferably 10 to 200 microns, with 20 to 100 microns being more preferable.

Subsequently, a porous PTFE film structure is wrapped as the fourth layer material over the airtight material of the third layer produced as described above. For the porous PTFE film structure that can be used in this case, those listed above can be used, and the wrapping method of the film can be either the longitudinal fashion or helical fashion. The thickness of the fourth layer is 50 to 500 microns, with 100 to 200 microns being further desirable.

The tube with the third and fourth layers applied over the base tube as described above is heated to a temperature that melts the synthetic resin used as the airtight material of the third layer, generally 200° to 400° C., preferably to a temperature of 330° to 390° C. When said heat treatment is performed, a multilayered tube with firmly bonded layers can be produced. Also, when the third layer and fourth layer are produced over the base tube, each layer may be bonded to the other layers with an adhesive.

In the product tube with a four-layered structure produced by depositing a third and fourth layer over the base tube by the method described above, when a material with a greater modulus than that of the porous PTFE structure, for example, a fluororubber, is used for the third layer, and a porous PTFE structure is used for the fourth layer, the torsion resistance is drastically improved and kinking is greatly eliminated compared with the base tube.

In the flexible, multilayered tube with the two-layered structure, it is possible to form a third layer over the outer peripheral surface of said tube to produce a three-layered tube structure. In this case, for the third layer material, the non-porous PTFE film structures described for the first layer can be used as well. In the tube produced by the method described above, the inner surface and the outer surface of the tube are smooth, and the sliding property is excellent. Furthermore, the stain resistance, antifungal properties, and resistance to the adsorption of organic materials are superior.

The flexible, multilayered tube of the present invention is especially effective as a medical tube. As a medical tube in this case, a body-fluid tube, forceps channeling tube, etc., can be mentioned. For said medical tubes, superior airtightness, watertightness, high flexibility, bending properties, and flexibility, as well as superior smoothness on the inner wall, stain resistance, antifungal properties, and resistance to the adsorption of organic materials are required. The tube of the present invention satisfies these requirements and is suitable for use as a medical tube. When the tube of the present invention is used as a medical tube, the inner diameter is 1 to 10 mm, preferably 2 to 6 mm. Also, it is desirable to set the thickness of the first layer to preferably less than 50 microns, and more preferably 5 to 30 microns, and the thickness of the second layer to less than 2 mm, preferably 0.2 to 0.8 mm.

Furthermore, it is desirable to set the thickness of the first layer at 1/1000 to 1/2, preferably 1/100 to 1/3, of the combined thickness of the first layer and second layer.

The flexible, multilayered tube of the present invention is especially suitable for the suction tube in a videoimage endoscope or a conduit-forming tube.

Figure 11:
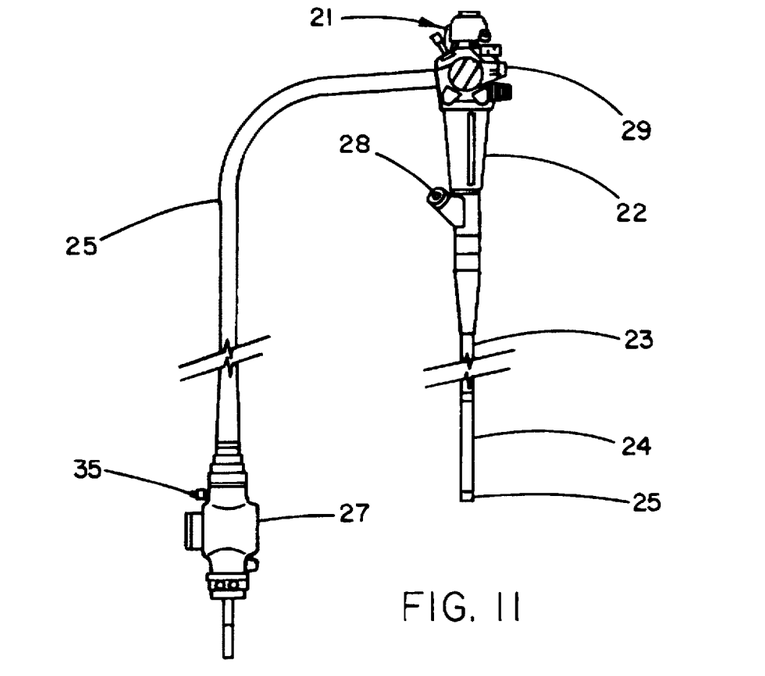
FIG. 11 is a schematic view that shows a videoimage endoscope.
Figure 12:
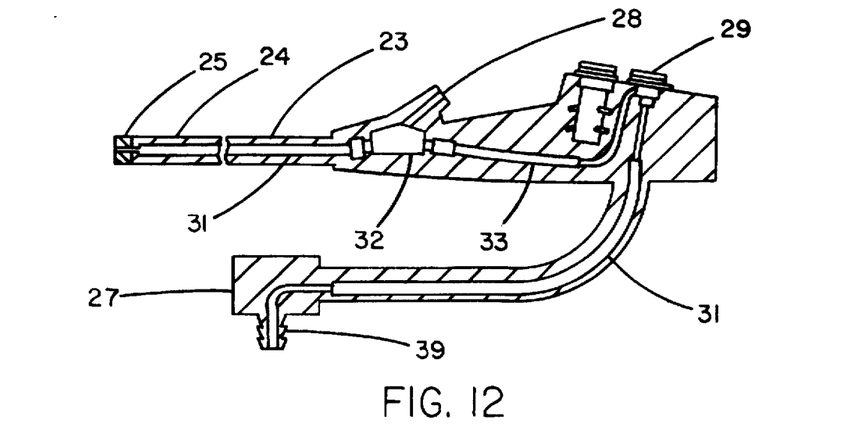
FIG. 12 shows the structure of a conduit used for suction and the insertion of a treatment device inside the videoimage endoscope.

A schematic explanatory view of the videoimage endoscope is shown in FIG. 11. The explanatory view of the structure of the conduit for suction and treatment insertion device inside the videoimage endoscope are shown in FIG. 12. An example of the connection structure of the conduit is shown in FIG. 13 and FIG. 14.

As shown in FIG. 11, the videoimage endoscope device 21 is comprised of the final control element 22, insertion part 23, curvature 24, end structural unit 25, universal code 26, and connector 27. It is used with an endoscope image-control device, monitor, light source, and suction device, which are not included in the figure. The treatment insertion port 28, suction switch, and control unit 29 are installed in the final control element 22, and the suction tube attachment nozzle 30 used for connecting with the suction device, which is the external device, is installed on the connector 27.

FIG. 12 is an explanatory view that shows the suction inside the videoimage endoscope device, and the structure of the conduit for the treatment insertion device. As shown in the figure, one end of the first suction tube 31 installed inside the insertion 23 and curvature 24 is fastened to the end structural unit 25 via a pipe, with the detail being as shown in FIG. 13. The other end of the first suction tube 31 is connected to the first opening of the branch 32 having three openings, each connected to each other and installed inside the final control element 22, with the detail being shown in FIG. 14. The second opening of the branch 32 is connected to the treatment insertion port 28. The third opening of the branch 32 is connected to the first opening of the suction switch control unit 29 via suction tube 33. The second opening of the suction switch control unit 29 is connected to the third suction tube via nozzle 30 of suction tube 34. The multilayered tube of the present invention can be used for the first suction tube 31, which requires the highest flexibility, and the multilayered tube of the present invention can be further used for the second suction tube 33, with the third suction tube 34 being used as needed.

Figure 13:
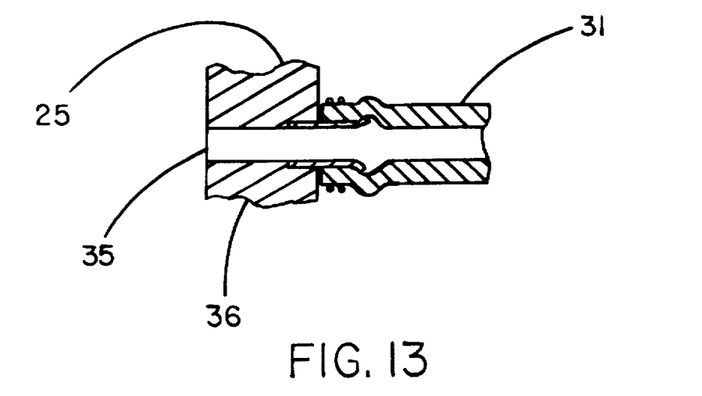
FIG. 13 shows one example of the connection structure of the conduit.
Figure 14:
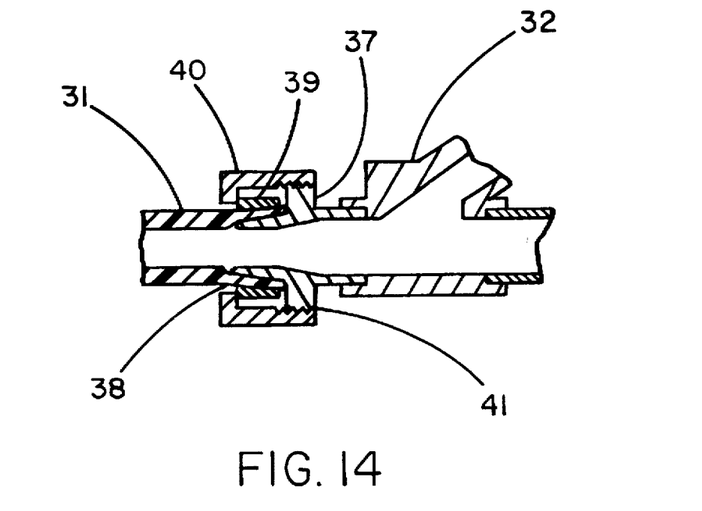
FIG. 14 shows a different example of the connection structure of the conduit.

FIG. 13 shows the connector area of the first suction tube 31, and the end structural unit 25. In this case, a through-pore 35 is provided at the end structural unit 25, with pipe 36 being attached with an adhesive or soldering. Also, the first suction tube 31 is bonded to pipe 36. One end of pipe 36 is tapered to prevent the tube coming off, and the hooking end of the treatment device is inserted into the tube. Incidentally, when a soft tube and a hard tube are connected, a sharp bend is formed in the connecting area when the endoscope is bent. In order to prevent said problem, the end of first suction tube 31 is subjected to a treatment to increase the rigidity, with an area having a medium degree of hardness being provided to form a smooth bending shape. For said treatment used to increase the rigidity, for example, a heat treatment is performed for the end to convert the porous structure of the second layer into a non-porous structure, or a material such as impregnated into the end of the second layer to convert the porous structure into a non-porous structure. Furthermore, the fluorine on the surface of the first layer of the tube is freed and polarized by means of a chemical reaction with a surface-treatment solution produced by dispersing metallic sodium in naphthalene, or plasma radiation is provided to increase the roughness to further improve the bonding between pipe 36 and the first suction tube 31. As a different method used to increase the bonding of pipe 36 and the first suction tube 31, a fishing gut line is wrapped around the joint of the pipe 36, and the first suction tube 31 over the tube, then the fishing gut line is coated with an adhesive.

FIG. 14 shows the connecting area of the other end of first suction tube 31 and the first opening of branch 32. In this case, the outer peripheral surface of the tip of connection material 37, inserted into the end of the branch 32, has a tapered surface 38. On the tapered surface, the first suction tube 31 with tapered ring 39 and the set screw 40 is coated, the set screw 40 is placed in threaded part 41 of the connecting material 37, and the other end of the first suction tube 31 and the first opening of branch 32 are connected.

As described above, the multilayered tube of the present invention can be used as the suction tube in the videoimage endoscope. In addition, it can be used for the suction tube of any endoscope, for example, an endoscope that uses fiber optics instead of the videoimage endoscope for image transmission and endoscopes having a hard or semi-hard insertion part.

Also, the multilayered tube of the present invention can be used as a storage tube, such as a drain tube. For tubes used for this purpose, it is desirable to use one having a third layer comprised of the same material used for the first layer on the outside of the tube comprised of said first and second layers. Also, for the third layer, other materials with a high biocompatibility can be used. Furthermore, when the porous structure is converted to a non-porous structure by subjecting the end of the tube to a treatment that increases the rigidity described above, a multilayered tube having properties that prevent the adsorption of organic materials over the entire surface of the tube can be produced.

EXAMPLES

In the following, the present invention is further explained with application examples.

Application Example 1

A biaxially drawn, nonbaked porous PTFE film having a micropore diameter of 0.2 microns, porosity of 70%, and thickness of 25 microns was stretched to form a non-porous film structure with a thickness of 7 microns at ambient temperature using rollers. It was confirmed that the non-porous film produced by said rolling method had a Gurley No. greater than 500,000 sec when measured by the air permeability and smoothness tester of the Oken type, and that it was virtually an airtight material.

Subsequently, two strips of the non-porous film (width of 20 mm) produced were wrapped around a stainless steel pipe with a diameter of 3.7 mm in a spiral fashion. A uniaxially drawn nonbaked porous PTFE film (width of 84 mm, the drawing direction and length direction are the same) with a micropore diameter of 5 microns, a porosity of 30%, and a thickness of 100 microns was then wrapped around said surface in a longitudinal fashion to produce 6 wraps.

Baking of the product wrapped with the PTFE film was done at 360° C. for 10 min; it was then cooled, and the stainless steel pipe was pulled out of the wrapped material. A multilayered tube consisting of a first layer comprised of a non-porous PTFE film structure and a second layer comprised of a porous PTFE film structure was then produced.

When the multilayered tube produced was bent at a bending radius of 10 mm, kinking did not occur, and the inner surface was smooth and stain resistant. When the inner surface was coated with an oil-based marker pen and wiped clean, the ink was completely removed. Also, when the tube was bent 10,000 times at a radius of curvature of 10 mm, no external change was observed, and the tube was free of destruction with an excellent flexibility. The 10,000 times bending test was performed by bending the tube back and forth at a radius of 10 mm while one end of the tube was immobilized, counting the cycle as one time. The cycle was repeated 10,000 times, then the deformation of the tube, rupture, changes in the surface appearance, and leakage of air were confirmed. The same method was used in the following application examples.

Application Example 2

A nonbaked, uniaxially drawn porous PTFE film with a micropore diameter of 1 micron, porosity of 65%, and thickness of 50 microns was placed between aluminum foil sheets and rolled with rollers at 350° C. to form a non-porous film structure with a thickness of 33 microns, then the aluminum foil was removed. When measurement of the non-porous film structure was performed by the air permeability and smoothness tester of the Oken type, it was confirmed that the non-porous film produced by said rolling method had a Gurley No. greater than 500,000 sec and was virtually an airtight material.

Subsequently, the non-porous film (width of 20 mm) produced was wrapped around a stainless steel pipe with a diameter of 4.2 mm to produce 1.25 wraps in the longitudinal fashion. A uniaxially drawn, nonbaked, porous PTFE film (width of 405 mm, the drawing direction and the length direction are the same) with a micropore diameter of 10 microns, porosity of 60%, and thickness of 50 microns was wrapped around said surface in a longitudinal fashion to produce 12 wraps.

Baking of the product wrapped with the PTFE film was done at 360° C. for 20 min. It was cooled and the stainless steel pipe was pulled out of the wrapped material, producing a multilayered tube consisting of a first layer comprised of a non-porous PTFE film structure and a second layer comprised of a porous PTFE film structure.

When the multilayered tube produced was bent at a bending radius of 10 mm, kinking did not occur, and the inner surface was smooth and stain resistant. When the inner surface was coated with an oil-based marker pen and wiped clean, the ink was completely removed. Also, when the tube was bent 10,000 times at a radius of curvature of 10 mm, no external changes were observed, the tube was free of destruction, and the flexibility was excellent.

Application Example 3

A non-baked, biaxially drawn, porous PTFE film with a micropore diameter of 0.2 microns, porosity of 70%, and thickness of 60 microns was wrapped around the outer peripheral surface of a stainless steel pipe with a diameter of 3 mm in longitudinal fashion to form 1.25 wraps. The wrapped material was then passed through one end of a stainless steel die with an inner diameter of 3.05 mm and pulled out from the other end. In this manner, the wrapped material was firmly compressed, and the porous PTFE film structure with a thickness of 60 microns was converted to a non-porous film structure with a thickness of 40 microns.

Subsequently, a non-baked, uniaxially drawn, porous PTFE film (width of 70 mm, the drawing direction and the longitudinal direction are the same) with a micropore diameter of 10 microns, porosity of 60%, and thickness of 100 microns was further wrapped over said layer in longitudinal fashion to produce 4 wraps.

Baking of the product wrapped with the PTFE film was then done at 360° C. for 15 min. It was cooled, and the stainless steel pipe was pulled out from the wrapped material producing a multilayered tube comprised of PTFE film. When measurement of the tube was performed with the air permeability and smoothness tester of the Oken type, it was confirmed that the tube produced had a Gurley No. greater than 500,000 sec and was virtually an airtight material. Furthermore, when the tube was cut in the circumferential direction and the cross section was examined by SEM, it was confirmed that the first layer was a non-porous structure and the second layer was a porous structure.

When the multilayered tube produced was bent at a bending radius of 10 mm as described above, kinking did not occur and the inner surface was smooth and stain resistant.

When the inner surface was coated with an oil-based marker pen and wiped clean, the ink was completely removed. Also, when the tube was bent 10,000 times at a radius of curvature of 10 mm, no external changes were observed, it was free of destruction, and the flexibility was excellent.

Application Example 4

A fluoro-rubber solution was coated onto the outer peripheral surface of the multilayered tube with a core material comprised of a stainless steel pipe produced in Application Example 3, after the baking treatment, to produce a fluoro-rubber layer with a thickness of 50 microns as the third layer. A nonbaked, uniaxially drawn PTFE tape (width of 21 mm) with a micropore diameter of 10 microns, porosity of 60%, and thickness of 80 microns was wrapped in a spiral fashion to form two wraps as the fourth layer at a tape pitch of 27 mm, baking was done at 380° C. for 3 min to produce the fourth layer (thickness of 160 microns), and a multilayered tube with a total film thickness of 0.5 mm was produced.

When the multilayered tube produced was bent at a bending radius of 10 mm as described above, kinking did not occur and the flexibility was superior. Also, the inner surface was smooth and stain resistant; when the inner surface was coated with an oilbased marker pen and wiped clean, the ink was completely removed. Also, when the tube was bent 10,000 times at a radius of curvature of 10 mm, no external changes were observed, it was free of destruction, and the flexibility was excellent.

Application Example 5

An extruded film with a thickness of 50 microns was dried, producing a PTFE film, then said film was wrapped around a stainless steel pipe with a diameter of 3.2 mm in longitudinal fashion to form 1.25 wraps. A nonbaked, uniaxially drawn PTFE film (width of 9.5 mm) with a micropore diameter of 5 microns, porosity of 30 microns, and thickness of 100 microns was further wrapped in a spiral fashion to produce 6 wraps at a wrapping pitch of 20 mm.

Baking of the product wrapped with the PTFE film was done at 360° C. for 10 min, it was cooled, and the stainless steel pipe was pulled out from the wrapped material. A multilayered tube having a first layer comprised of a nonporous PTFE layer and a second layer comprised of a porous PTFE layer was thus produced. When the tube produced was bent at a bending radius of 10 mm as described above, kinking did not occur and the inner surface was smooth and stain resistant. When the inner surface was coated with an oilbased marker pen and wiped clean, the ink was completely removed. Also, when the tube was bent 10,000 times at a radius of curvature of 10 mm, no external changes were observed, it was free of destruction, and the flexibility was excellent.

Application Example 6

A porous PTFE film (width: 28 mm) produced by drying an extruded film with a thickness of 30 microns was laminated with a PFA tape (width: 29 mm) with a thickness of 12.5 microns, producing a two-layered PFA tape with a 0.5 mm flange sticking out from both sides.

The two-layered tape produced was wrapped around the outer peripheral surface of a stainless steel pipe with a diameter of 2.95 mm to produce 3 wraps in such a manner that the surface of the PTFE was on the inside. The PFA tape alone was completely exposed on the outer peripheral surface of the wrapped material, at the same time, the PFA tape with a width of 0.5 mm was exposed on the edge of the PTFE tape in the form of a spiral on the inner surface.

Subsequently, a nonbaked, uniaxially drawn, porous PTFE film with a micropore diameter of 10 microns, porosity of 55%, and thickness of 90 microns was wrapped around the outer peripheral surface of the material in a spiral fashion to produce 6 wraps.

Baking of said wrapped material was done at 360° C. for 10 min, thus a multilayered tube having adhesive layers between the PTFE films that comprise the first layer and between the first layer and second layer was produced.

While the core material was still in position, a fluororubber solution was coated onto the outer peripheral surface of the multilayered tube and dried, producing a fluoro-rubber layer with a thickness of 30 microns as a third layer. A nonbaked, uniaxially drawn porous tape (width: 25 mm) with a micropore diameter of 10 microns, porosity of 60%, and thickness of 50 microns was wrapped in a spiral fashion to produce 2 wraps over said layer; baking was then performed at 360° C. for 8 min. Thus, a porous PTFE layer with a thickness of 100 microns was produced as the fourth layer. After cooling, the stainless steel pipe was removed from the wrapped material, producing a four-layered tube structure with an inner diameter of 2.8 mm and a thickness of 0.6 mm.

When the multilayered tube produced was bent at a bending radius of 10 mm as described above, kinking did not occur and the inner surface was smooth and stain resistant. When the inner surface was coated with an oil-based marker pen, and wiped clean, the ink was completely removed. Furthermore, the groove produced at the overlap of the PTFE tape was filled with the molten PFA, producing a smooth inner surface. The cleaning time required for removing contaminants was thus drastically reduced. Furthermore, when the tube was subjected to a distortion test of ±90° 1000 times in addition to the bending test of 10,000 times, destruction did not occur in the abrasion test performed for the non-porous PTFE layer with the treatment devices used for endoscopes. When an internal pressure of 1.5 kg/cm$^2$ was applied using air under water after said tests, leaking of air from the wall of the tube did not occur, exhibiting complete airtightness.

Application Example 7

A dispersion (concentration of 20% by weight) produced by dispersing a fine powder of FEP (grain diameter 0.2 to 0.4 microns) in water was coated onto one side of a PTFE film tape (width: 21.5 mm) produced by extruding a film with a thickness of 30 microns and drying. The tape was wrapped around the outer peripheral surface of a stainless steel pipe with a diameter of 3.45 mm in a spiral fashion to form 2 wraps with the non-coated surface facing inward. A tape treated in the same manner and having the same size was further wrapped over the outer peripheral surface of said layer in a spiral fashion to form 2 wraps, producing a total of 4 wraps. In this case, the second tape was wrapped at an angle opposite to the first tape so that the wraps crossed. A non-baked, uniaxially drawn, porous PTFE film with a micropore diameter of 10 microns, porosity of 60%, and thickness of 90 microns was wrapped around the outer peripheral surface of said material to produce 4 wraps in a spiral fashion. Four wraps were then made in the opposite direction, for a total of 8 wraps. Baking of the wrapped material produced was done at 355° C. for 10 min and it was cooled; the stainless steel pipe was then pulled out. A multilayered tube having a first layer comprised of a nonporous PTFE layer firmly bonded with an adhesive comprised of FEP, and a second layer comprised of a porous PTFE layer structure having an inner diameter of 3.2 mm and a thickness of 0.6 mm. was thus produced.

In the product tube formed above, the wrapping direction of the film that comprises the first layer is crossed, and the wrapping direction of the film that comprises the second layer is also crossed. Therefore, the orientation of the film strength generated at the time of extrusion or stretching of the film during the film production is eliminated, and the orientation of the strength of the tube as a whole is low. The tube exhibits excellent durability when the distortion test is performed at ±90°;kinking does not occur even after a distortion test of 2000 times. Also, the inner surface of the tube is smooth and the stain resistance is superior. Also, when the inner surface is coated with an oil-based marker pen and wiped clean, the ink is completely removed. Furthermore, when the tube is subjected to a bending test of 10,000 times, no external changes are observed and destruction does not occur. When an internal pressure of 1.5 kg/cm$^2$ is applied using air under water after leakage of the air from the wall of the tube does not occur and the total impermeability (airtightness) of the material is confirmed.

We claim:
1. A flexible, multilayered tube comprising
   a) a first layer consisting essentially of a non-porous structure comprised of polytetrafluoroethylene, said non-porous structure having a thickness of less than 300 micrometers and having an outer peripheral surface: and
   b) a second layer comprised of a porous polytetrafluoroethylene structure laminated onto the outer peripheral surface of said first layer, and having a porosity of about 30 to 70 percent;
   wherein the thickness of the first layer is 1/1000 to 1/2 of the combined thickness of the first layer and second layer.

2. A flexible, multilayered tube described in claim 1 wherein the first layer and second layer are laminated by fusion under heat.

3. A flexible, multilayered tube described in claim 1 wherein the first layer and second layer are laminated via an adhesive interlayer.

4. The flexible, multilayered tube described in claim 3, wherein the adhesive interlayer is a thermoplastic fluorine resin.

5. The flexible, multilayered tube described in claim 1, wherein the first layer comprises at least two layers of polytetrafluoroethylene laminated by an adhesive.

6. The flexible, multilayered tube described in claim 2, wherein the first layer comprises at least two layers of polytetrafluoroethylene laminated by an adhesive.

7. The flexible, multilayered tube described in claim 3, wherein the first layer comprises at least two layers of polytetrafluoroethylene laminated by an adhesive.

8. The flexible, multilayered tube described in claim 5, wherein the adhesive is a thermoplastic fluorine resin.

9. The flexible, multilayered tube described in claim 6, wherein the adhesive is a thermoplastic fluorine resin.

10. The flexible, multilayered tube described in claim 7, wherein the adhesive is a thermoplastic fluorine resin.

11. The flexible, multilayered tube described in claim 1, wherein the first layer comprises porous polytetrafluoroethylene film made non-porous with a thermoplastic fluorine resin.

12. The flexible, multilayered tube described in claim 11 wherein the thermoplastic fluorine resin is a tetrafluoroethylene/perfluoroalkyl vinyl ether copolymer.

13. The flexible, multilayered tube described in claim 11 wherein the thermoplastic fluorine resin is fluorinated ethylene propylene.

14. The flexible, multilayered tube described in claim 1, with a fourth layer comprised of porous polytetrafluoroethylene laminated onto the outer peripheral surface of the second layer via a third layer consisting of an airtight material.

15. The flexible, multilayered tube described in claim 2, with a fourth layer comprised of porous polytetrafluoroethylene laminated onto the outer peripheral surface of the second layer via a third layer consisting of an airtight material.

16. The flexible, multilayered tube described in claim 3, with a fourth layer comprised of porous polytetrafluoroethylene laminated onto the outer peripheral surface of the second layer via a third layer consisting of an airtight material.

17. A medical tubing comprising the flexible, multilayered tube described in claim 1.

18. A medical tubing comprising the flexible, multilayered tube described in claim 2.

19. A medical tubing comprising the flexible, multilayered tube described in claim 3.

20. A medical tubing comprising the flexible, multilayered tube described in claim 14.

21. A tube for an endoscope comprising the flexible, multilayered tube described in claim 1.

22. A tube for an endoscope comprising the flexible, multilayered tube described in claim 2.

23. A tube for an endoscope comprising the flexible, multilayered tube described in claim 3.

24. A tube for an endoscope comprising the flexible, multilayered tube described in claim 14.

25. A flexible, multi-layered tube comprising;
   a) a first, inner layer comprising a tubular polytetrafluoroethylene structure having inner and outer surfaces and a substantially uniform thickness of less than 300 microns therebetween, wherein the structure is substantially non-porous between the inner and outer surfaces of the first, inner layer; and
   b) a second layer laminated onto the outer surface of the first, inner layer, said second layer comprising a tubular polytetrafluoroethylene structure having inner and outer surfaces and further having substantially uniform porosity of about 30 to 70 percent between the inner and outer surfaces of the second layer;
   wherein the first and second layers have a combined thickness and the substantially uniform thickness of the first layer is 1/1000 to 1/2 of the combined thickness of the first and second layers.

* * * * *

UNITED STATES PATENT AND TRADEMARK OFFICE
CERTIFICATE OF CORRECTION

PATENT NO. : 5,789,047
DATED : August 4, 1998
INVENTOR(S) : Fumihiro Sasaki, Hiroshi Shinmen, Akira Suzuki and Keiichi Arai It is certified that error appears in the above-identified patent and that said Letters Patent is hereby corrected as shown below:

In Claim 1 at column 17 line 33 before the word "porosity" insert --substantially uniform--.
In Claim 1 at column 17 line 34 after the phrase "the thickness of the first layer is" insert --substantially uniform and--.

Signed and Sealed this

Seventeenth Day of November, 1998

Attest:

BRUCE LEHMAN

Attesting Officer   Commissioner of Patents and Trademarks